(12) United States Patent
Gemborys et al.

(10) Patent No.: US 9,956,323 B2
(45) Date of Patent: May 1, 2018

(54) MEDICAL DEVICES FOR LOCAL BIOACTIVE DELIVERY

(71) Applicant: Cook Medical Technologies LLC, Bloomington, IN (US)

(72) Inventors: Colleen Gemborys, Bloomington, IN (US); Steve Pendleton, Spencer, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 84 days.

(21) Appl. No.: 14/971,392

(22) Filed: Dec. 16, 2015

(65) Prior Publication Data

US 2016/0175495 A1  Jun. 23, 2016

Related U.S. Application Data

(60) Provisional application No. 62/093,804, filed on Dec. 18, 2014.

(51) Int. Cl.
| | |
|---|---|
| A61F 2/00 | (2006.01) |
| A61F 13/00 | (2006.01) |
| A61M 31/00 | (2006.01) |
| A61L 31/16 | (2006.01) |
| A61L 31/14 | (2006.01) |
| A61L 31/04 | (2006.01) |

(52) U.S. Cl.
CPC ............. *A61L 31/16* (2013.01); *A61L 31/042* (2013.01); *A61L 31/148* (2013.01)

(58) Field of Classification Search
None
See application file for complete search history.

(56) References Cited

U.S. PATENT DOCUMENTS

| | | | |
|---|---|---|---|
| 5,114,719 | A | 5/1992 | Sabel et al. |
| 5,567,488 | A | 10/1996 | Allen et al. |
| 6,096,070 | A | 8/2000 | Ragheb et al. |
| 6,596,298 | B2 | 7/2003 | Leung et al. |
| 8,658,196 | B2 | 2/2014 | Janis |
| 8,882,850 | B2 | 11/2014 | Hiles et al. |
| 2003/0118649 | A1 | 6/2003 | Gao et al. |
| 2006/0134211 | A1 | 6/2006 | Lien et al. |
| 2007/0020469 | A1 | 1/2007 | Wood et al. |
| 2008/0220029 | A1 | 9/2008 | Ng et al. |

(Continued)

FOREIGN PATENT DOCUMENTS

| | | |
|---|---|---|
| WO | WO2006023261 | 3/2006 |
| WO | WO2010021973 | 2/2010 |
| WO | WO2012142318 | 10/2012 |

*Primary Examiner* — Jeffrey T. Palenik
(74) *Attorney, Agent, or Firm* — Buchanan Van Tuinen LLC (57) ABSTRACT

Medical devices for local bioactive delivery are described. A medical device includes a first biodegradable layer, a second biodegradable layer, and a bioactive disposed between the first and second biodegradable layers. The first and second biodegradable layers are positioned such that a surface of the first biodegradable layer faces a surface of the second biodegradable layer and such that a peripheral portion of one biodegradable layer is folded over a peripheral portion of the other biodegradable layer. Methods of making medical devices and methods of using medical devices are also described.

20 Claims, 5 Drawing Sheets

(56) References Cited

U.S. PATENT DOCUMENTS

| | | |
|---|---|---|
| 2008/0220039 A1 | 9/2008 | Sherman |
| 2009/0098183 A1 | 4/2009 | Detamore et al. |
| 2009/0098192 A1 | 4/2009 | Fuisz |
| 2010/0280452 A1 | 11/2010 | Chen et al. |
| 2011/0189259 A1 | 8/2011 | Vasisht et al. |
| 2011/0200715 A1* | 8/2011 | Fuisz ................ A23F 5/36 426/103 |
| 2014/0180398 A1 | 6/2014 | Milner et al. |

* cited by examiner

MEDICAL DEVICES FOR LOCAL BIOACTIVE DELIVERY

FIELD

The disclosure relates generally to the field of medical devices. More particularly, the disclosure relates to the field of medical devices suitable for use in delivery of a bioactive agent to a point of treatment in or on the body of an animal, such as a human being, and methods of making such medical devices.

BACKGROUND

Cancer is a leading cause of death worldwide. Current treatments for many cancers include systemic administration of bioactive agents that have negative side effects and that can have significant impact on a patient's quality of life. Local delivery of bioactive agents directly to a point of treatment may provide a route of administration that avoids the side effects and quality of life implications associated with systemic delivery of cancer treatment agents and other bioactive agents. The art does not provide, however, suitable medical devices for achieving suitable local dosages while avoiding systemic spread of the bioactive agent.

A need exists, therefore, for improved medical devices for delivering a bioactive to a point of treatment, and for methods of making and using such medical devices.

BRIEF SUMMARY OF SELECTED EXAMPLES

Several medical devices are described and illustrated herein. An example medical device comprises a first biodegradable layer having a first peripheral edge, first and second opposing surfaces, and a first peripheral portion including portions of the first and second opposing surfaces and a portion of the first peripheral edge, the first layer having a first area; a second biodegradable layer having a second peripheral edge, third and fourth opposing surfaces, and a second peripheral portion including portions of the third and fourth opposing surfaces and a portion of the second peripheral edge, the second layer having a second area that is less than the first area; the first and second biodegradable layers positioned such that the second surface faces the third surface; the first peripheral portion folded over the second peripheral portion such that a portion of the second surface contacts a portion of the fourth surface; and a bioactive disposed between the first and second biodegradable layers.

Another example medical device comprises a first biodegradable layer having a first peripheral edge, first and second opposing surfaces, and a first peripheral portion including portions of the first and second opposing surfaces and the entire first peripheral edge, the first layer having a first area; a second biodegradable layer having a second peripheral edge, third and fourth opposing surfaces, and a second peripheral portion including portions of the third and fourth opposing surfaces and the entire second peripheral edge, the second layer having a second area that is less than the first area; the first and second biodegradable layers positioned such that the second surface faces the third surface; the first peripheral portion folded over the second peripheral portion such that a portion of the second surface contacts a portion of the fourth surface; and a bioactive disposed between the first and second layers.

Another example medical device comprises a first biodegradable layer having a first peripheral edge, first and second opposing surfaces, and a first peripheral portion including portions of the first and second opposing surfaces and the entire first peripheral edge, the first layer having a first area; a second biodegradable layer having a second peripheral edge, third and fourth opposing surfaces, and a second peripheral portion including portions of the third and fourth opposing surfaces and the entire second peripheral edge, the second layer having a second area that is less than the first area; the first and second biodegradable layers positioned such that the second surface contacts the third surface; the first peripheral portion folded over the second peripheral portion such that a portion of the second surface contacts a portion of the fourth surface; and a bioactive disposed between the first and second layers, the bioactive comprising a powder.

Several methods of making a medical device are described and illustrated herein. An example method comprises disposing a bioactive onto a first biodegradable layer; disposing a second biodegradable layer onto the bioactive and first biodegradable layer; and securing the first and second biodegradable layers to each other. One optional step comprises forming a triple laminate structure on the periphery of the first and second biodegradable layers.

Additional understanding of the claimed medical devices and methods can be obtained by reviewing the description of selected examples, below, with reference to the appended drawings.

DETAILED DESCRIPTION OF SELECTED EXAMPLES

The following detailed description and appended drawings describe and illustrate various examples of the invention. The description and drawings serve to enable one skilled in the art to make and use the inventive medical devices and methods; they are not intended to limit the scope of the invention or the protection sought in any manner. The invention is capable of being practiced or carried out in various ways; the examples described herein are exemplary in nature and are not exhaustive. As such, the language used in the description of examples is to be given the broadest possible scope and meaning.

Relevant background information is available in U.S. Pat. No. 8,658,196 to Janis on Feb. 25, 2014 for "GRAFT MATERIALS AND METHODS FOR STAGED DELIVERY OF BIOACTIVE COMPONENTS" and United States Published Application No. 2014/0180398 to Milner et al. for "BIOABSORBABLE MEDICAL DEVICES AND METH- ODS OF USE THEREOF", the contents of which are expressly incorporated into this disclosure in their entirety.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular.

The following definitions are used throughout the disclosure: the term 'bioactive' and grammatically related terms refer to a substance that has a biological effect in an animal.

Figure 1:
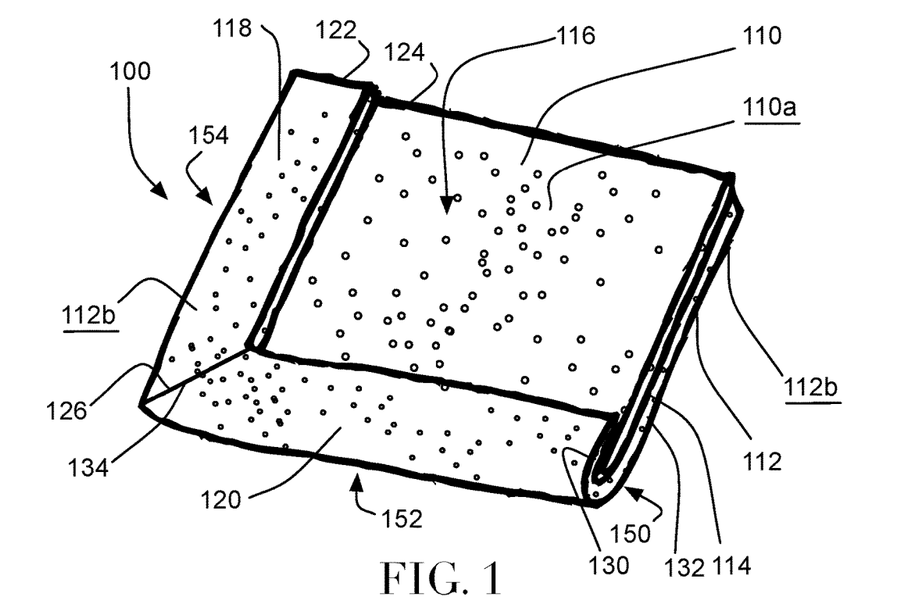
FIG. 1 is a perspective view of an example medical device.
Figure 2:
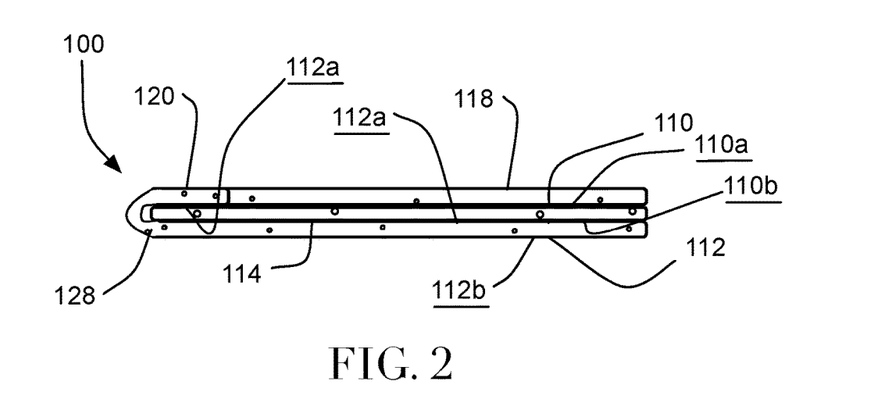
FIG. 2 is an end view of the medical device illustrated in FIG. 1.
Figure 3:
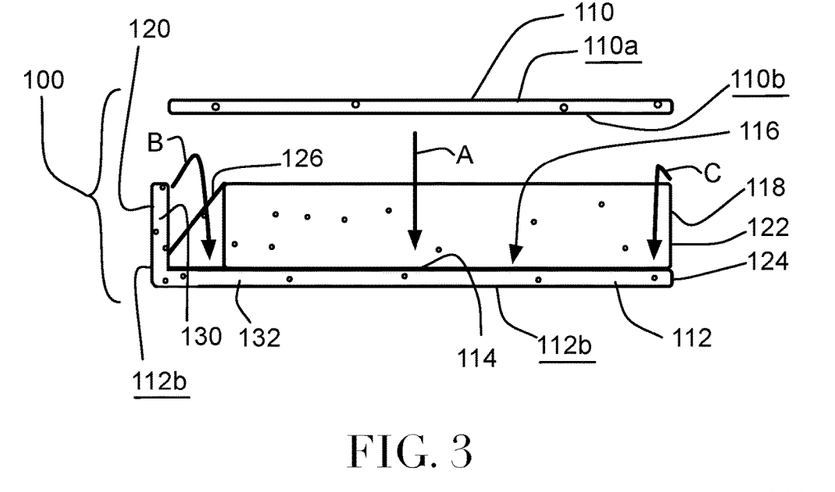
FIG. 3 is an exploded view of the medical device illustrated in FIG. 1.

FIGS. 1 through 3 illustrate a first example medical device 100. The medical device 100 comprises first 110 and second 112 layers and a bioactive 114. The bioactive 114 is disposed between the first 110 and second 112 layers, effectively creating a sandwich structure. As described in detail below, the bioactive 114 can comprise a layer disposed between the first 110 and second 112 layers, or can comprise a solution or other form that is initially disposed between the first 110 and second 112 layers and that diffuses into the material of one or both of the layers 110, 112.

As described in detail below, the medical device 100 can be used as a temporary bioactive delivery device that degrades after a period of time. Accordingly, each of the first 110 and second 112 layers is formed of a biodegradable material. The layers 110, 112 can be formed of the same or different materials.

Any suitable biodegradable material can be used for the layers, and a skilled artisan will be able to select one or more suitable biodegradable materials for use in a particular medical device based on various considerations, including any desired size and/or configuration of the medical device, any desired directional release of the bioactive in the medical device, and any desired degradation timeline for the medical device. Example of suitable biodegradable materials for use in the first and second layers of medical devices according to embodiments include, but are not limited to, polyglycolic acid, polylactide, poly(dioxanone), poly(trimethylene carbonate) copolymers, and poly (ϵ-caprolactone) homopolymers and copolymers, polyanhydrides, polyorthoesters, polyphosphazenes, and other biodegradable polymers. Cellulose materials are also considered suitable.

The inventors have determined that carboxymethyl cellulose (CMC) is particularly well-suited for use in one or both layers of a medical device according to an embodiment at least because of its well-characterized nature. Hydroxylpropyl methyl cellulose (HMC) is also considered particularly well-suited for use in the inventive medical devices at least because of its well-characterized nature.

For medical devices in which the first and second layers are formed of different biodegradable materials, a skilled artisan will be able to select two suitable biodegradable materials for use in a particular medical device based on various considerations. For example, if a desired directional release of the bioactive in the medical device is desired, a first biodegradable material that degrades relatively quickly in vivo can be used as the first layer in the medical device and a second biodegradable material that degrades relatively slowly in vivo can be used as the second layer in the medical device. In a medical device having such a pair of layers, the first layer will degrade relatively quickly, resulting in release of the bioactive to the surrounding tissue at the point of treatment, while the second layer will degrade relatively slowly, effectively providing a barrier to release of the bioactive and conferring directionality onto the medical device.

The medical devices can have any suitable size, shape and configuration. Likewise, each of the layers in a particular medical device can have any suitable size, shape and configuration. A skilled artisan will be able to select an overall size, shape and configuration for a medical device according to a particular embodiment based on various considerations, including spatial properties of the point of treatment at which the medical device is intended to be used. Similarly, a skilled artisan will be able to select an overall size, shape and configuration for each of the layers in a medical device according to a particular embodiment based on various considerations, including the desired overall size, shape and configuration of the medical device and the size, shape and configuration of the other layer in the medical device.

Each of the layers in a medical device according to a particular embodiment can have any suitable thickness extending between the first and second surfaces, such as surfaces 110a and 110b for the first layer in the medical device 110 illustrated in FIGS. 1 through 3. Furthermore, in a particular medical device, the layers can have the same or different thicknesses. A skilled artisan will be able to select suitable thicknesses for each of the layers in a medical device according to a particular embodiment based on various considerations, including the bioactive or bioactives in the medical device, the nature of the material of which the layer is made, any desired release profile and/or dynamics for the bioactive or bioactives, and the spatial configuration of the point of treatment at which the medical device is intended to be used. Indeed, each layer in a medical device according to a particular embodiment can comprise a sheet, a film, or a thin film.

Each of the layers 110, 112 is advantageously flexible and capable of being physically manipulated, e.g., bent, curved, folded, twisted, etc., by hand. Having both layers 110, 112 have these properties allows a user to physically manipulate the medical device 100 at the time of treatment to accommodate any physical constraints or features of a particular point of treatment to achieve the desired localized delivery of the bioactive 114.

In the medical device 100 illustrated in FIGS. 1 through 3, the first layer 110 has a first surface 110a and a second surface 110b. Similarly, the second layer 112 has a first surface 112a and a second surface 112b. The first layer 110 is rectangular in shape. The second layer 112 has a rectangular main portion 116 and first 118 and second 120 tabs extending from the main portion 116. The first tab 118 has a first lateral edge 122 that is continuous with an adjacent lateral edge 124 of the rectangular portion 116 and a second lateral edge 126 that is not continuous with an adjacent lateral edge 128 of the rectangular portion 116. Similarly, the second tab 120 has a first lateral edge 130 that is continuous with an adjacent lateral edge 132 of the main portion 116 and a second lateral edge 134 that is not continuous with an adjacent lateral edge (not visible in the Figures) of the main portion 116. In the illustrated embodiment, each of the second lateral edge 126 of the first tab 118 and the second lateral edge 134 of the second tab 120 extends at a non-orthogonal angle to the respective adjacent edge of the main portion 116. This allows the second lateral edges 126, 134 to be disposed adjacent and in continuous contact with each other when the tabs 118, 120 are folded onto the first layer 110, as best illustrated in FIG. 1 and described in detail below.

As best illustrated in FIG. 3, the first surface 112a of the second layer 112 is larger than the second surface 110b of the first layer 110. This configuration allows the first layer 110 to be placed substantially onto the main portion 116 of the second layer 112, represented by arrow A in FIG. 3, leaving the tabs 118, 120 substantially free of the first layer until the tabs 118, 120 are folded over peripheral portions of the first layer 110, as indicated by the arrows B and C in FIG. 3. This manipulation of the layers 110, 112 and tabs 118, 120 produces the final device structure illustrated in FIGS. 1 and 2. In the final structure, the tabs 118, 120 are folded over the first layer 110 such that portions of the first surface 112a of the first layer 112, the portions on the tabs 118, 120, are disposed adjacent and in contact with portions of the first surface 110a of the first layer 110.

As best illustrated in FIG. 1, this structural configuration provides a triple laminate structure 150 for two continuous edges 152, 154 of the medical device 110. This structure is considered advantageous at least because it can provide lateral directionality to the release of the bioactive 114, particularly when the second layer 112 is formed of a material that degrades relatively more slowly than the material of the first layer 110. Furthermore, the triple laminate structure 150 provides a visual and tactile indicator that conveys information to a user of the medical device about any lateral directionality of the release profile of the medical device 100. Also, as the medical device is well-suited for gross physical manipulation at a point of treatment, such as hand manipulation to conform to a tissue, cavity or space, the triple laminate structure confers a physical feature onto the medical device 110 that can facilitate handling and manipulation. This can be particularly advantageous for handling and manipulation of the medical device 100 because the user of the device is expected to be donning examination and/or surgical gloves at the time of use.

The bioactive used in a particular method can comprise a single bioactive, two bioactives, or a plurality of bioactives. When more than one bioactive is used, the bioactives can be mixed prior to being disposed on another component of the medical device according to an embodiment, or can be separately disposed on components of a medical device according to an embodiment. For example, a layer or a solution containing a first bioactive can be applied to the first layer 110 of a medical device 100, and a layer or solution containing a second bioactive can be applied to the second layer 112 of the medical device 100. The layers 110, 112 can then be brought together such that the two bioactives are both disposed between the layers 110, 112 in the final medical device 100 assembly.

Any suitable bioactive can be used in the methods and medical devices described herein. The specific bioactive, or bioactives, selected for any particular method or medical device will depend upon several considerations, including the desired effect and the type of treatment and/or procedure in which the medical device is intended to be used. Examples of suitable bioactives include anti-cancer agents, such as paclitaxel, tamoxifen citrate, and Taxol® or derivatives thereof; anthracyclines, such as doxorubicin; pyrimidine analogs, such as 5-fluorouracil; nucleoside analogs, such as gemcitabine; platinum-based antineoplastics, such as cisplatin, carboplatin, oxaliplatin, satraplatin, picoplatin, nedaplatin, triplatin, and lipoplatin; immunosuppressive agents, such as cyclosporine and sirolimus; and other anti-cancer chemotherapeutic agents. Monoclonal and polyclonal antibodies can also be used as a bioactive in the methods and medical devices described herein. For example, recombinant humanized angiogenesis inhibiting monoclonal antibodies, such as Bevacizumab, are suitable. Also, chimeric monoclonal antibodies that inhibit epidermal growth factor receptor (EGFR), such as Cetuximab, are suitable. Also, anti-idiotype tumor antigen epitope mirroring monoclonal antibodies, such as Abagovomab, are suitable. Other examples of bioactives that can be used in the methods and medical devices include, but are not limited to, heparin, covalent heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a tyrosine-kinase inhibitor, such as Imatinib; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; dexamethasone, dexamethasone sodium phosphate, dexamethasone acetate or another dexamethasone derivative, or another anti-inflammatory steroid or non-steroidal anti-inflammatory agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; 60Co, 192Ir, 32P, 111In, 90Y, 99mTc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a 14C-, 3H-, 131I-, 32P- or 36S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine betahydroxylase conjugated to saporin or other antibody target therapy agents; enalapril or other prodrugs; any endothelium progenitor cell attracting, binding and/or differentiating agents, including suitable chemoattractive agents and suitable polyclonal and monoclonal antibodies; cell migration inhibiting agents, such as smooth muscle cell migration inhibitors, such as Bamimistat, prolylhydrolase inhibitors, Probacol, c-proteinase inhibitors, halofuginone, and other suitable migration inhibitors; and gene therapy agents, and a mixture of any of these.

Two or more bioactives can be used when preparing a solution 102 for use in the method 100. For example, FOLFIRI, folinic acid with fluorouracil and irinotecan, is suitable for use as the bioactive in the methods and medical devices described herein. Also, FOLFOX, folinic acid with fluorouracil and oxaliplatin, is suitable for use as the bioactive in the methods and medical devices described herein.

Furthermore, the solution can be prepared in any suitable manner. Accordingly, any suitable fluid or fluids can be used when preparing the solution. A skilled artisan will be able to select an appropriate fluid for a method according to a particular method based on various considerations, including the nature of the bioactive or bioactives being used in the method. Examples of suitable fluids include water, such as Sterile Water for Injection USP, and alcohols, including ethanol and other alcohols. Also, any suitable techniques, processes, or steps can be used when preparing the solution, including heating, stirring, cooling, mixing and other suitable techniques, processes and steps.

One or more excipients can be included in the solution if desired. If included, any suitable excipient can be included, including sugars and inorganic compounds.

The inventors have determined that a combination of paclitaxel and carboplatin that is disposed between the layers of a medical device according to an embodiment is suitable for use as the bioactive in the medical device. Furthermore, the inventors have determined that a solution of paclitaxel in ethanol is suitable for use as the bioactive in a medical device according to an embodiment.

No matter which bioactive or bioactives are used in a medical device according to a particular embodiment, the bioactive or bioactives can be associated with the medical device in any suitable manner. In the medical device 100 illustrated in FIGS. 1 through 3, the bioactive 114 has been disposed between the layers 110, 112 in solution form, and the bioactive 114 has diffused into the material of the layers 110, 112 (represented by the open circles in the FIGS. 1 through 3). A solution containing the bioactive 114 can be disposed between the layers in any suitable manner, including by application to one surface of one of the layers, e.g., surface 112a of layer 112, followed by placement of layer 110 onto surface 112a of layer 112. Alternatively, a solution containing the bioactive 114 can applied to surface 110b of layer 110, followed by placement of layer 110 onto surface 112a of layer 112. Also alternatively, a solution containing the bioactive 114 can be applied to surface 110b of layer 110 and surface 112a of layer 112, followed by placement of layer 110 onto surface 112a of layer 112.

In the final assembled form, best illustrated in FIG. 1, layers 110, 112 of medical device 110 are secured to each other. The layers 110, 112 can be secured to each other in a variety of manners, such as by inclusion of an adhesive between the layers, crimping, inclusion of mechanical connectors, such as pins, clips, sutures or any other suitable mechanical connector, and any other suitable means for securing biodegradable layers to each other. If an additional component is included, such as a mechanical connector, it is considered advantageous that the additional component also be formed of a biodegradable material, such as a biodegradable suture. It is noted, too, that the physical properties of the layers in a medical device according to a particular embodiment may provide sufficient securement between the layers once the medical device is assembled into a final form such that additional elements and/or processing is not required.

Figure 4:
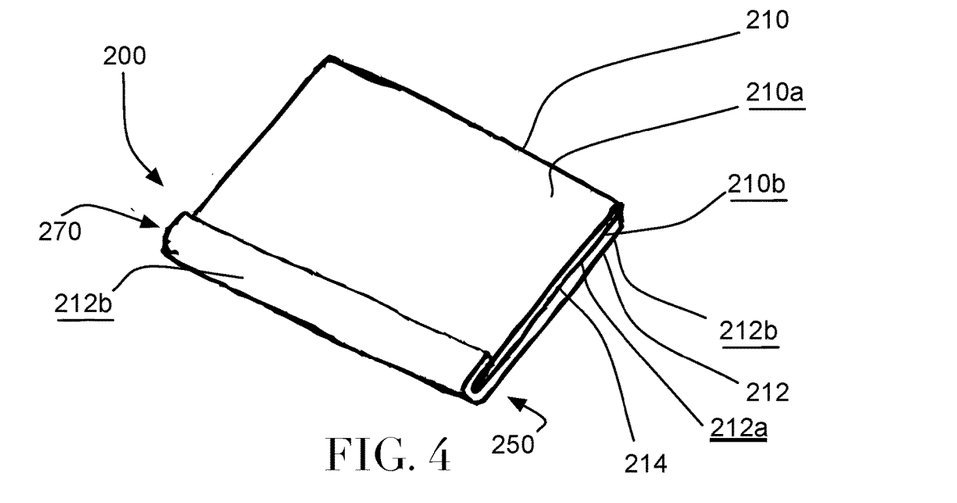
FIG. 4 is a perspective view of another example medical device.

FIG. 4 illustrates a second example medical device 200. The medical device 200 according to this embodiment is similar to the medical device 100 described above and illustrated in FIGS. 1 through 3, except as detailed below. Thus, medical device 200 comprises first 210 and second 212 layers and a bioactive 214 disposed between the layers 210, 212. The first layer 210 has a first surface 210a and a second surface 210b. Similarly, the second layer 212 has a first surface 212a and a second surface 212b. The first layer 210 is rectangular in shape. In this embodiment, the second layer 212 is also rectangular in shape. The second layer 212 is larger than the first layer 210 allowing a small portion 270 of the second layer 212 to be folded over a portion of the first layer 210 once the first layer 210 is disposed on the second layer 212. This structural configuration provides a triple laminate structure 250 for only a single edge 252 of the medical device 110.

The structure provided by a medical device having a triple laminate structure along only a single edge of the medical device may be advantageous for situations in which it is desirable to have a portion of the medical device that provides a structure that facilitates handling of the medical device and/or a structure that provides visual and tactile feedback of a directional release profile of the bioactive in the medical device, but also in which the point of treatment at which the medical is intended to be used has spatial concerns and/or limitations that prevent use of a bulkier structure, such as the medical device 100 illustrated in FIGS. 1 through 3.

In this embodiment, the bioactive 214 comprises a solid layer disposed between the layers 210, 212 in a "sandwich" arrangement. A paste, powder, gel, film, solution-containing solid, or other suitable form of the bioactive or bioactives can be used to achieve this structural arrangement. Furthermore, the bioactive 214 can be disposed between the layers 210, 212 in any suitable manner, including by application to one surface of one of the layers, e.g., surface 212a of layer 212, followed by placement of layer 210 onto surface 212a of layer 212. Alternatively, the bioactive 214 can applied to surface 210b of layer 210, followed by placement of layer 210 onto surface 212a of layer 212. Also alternatively, the bioactive 214 can be applied to surface 210b of layer 210 and surface 212a of layer 212, followed by placement of layer 210 onto surface 212a of layer 212.

Figure 5:
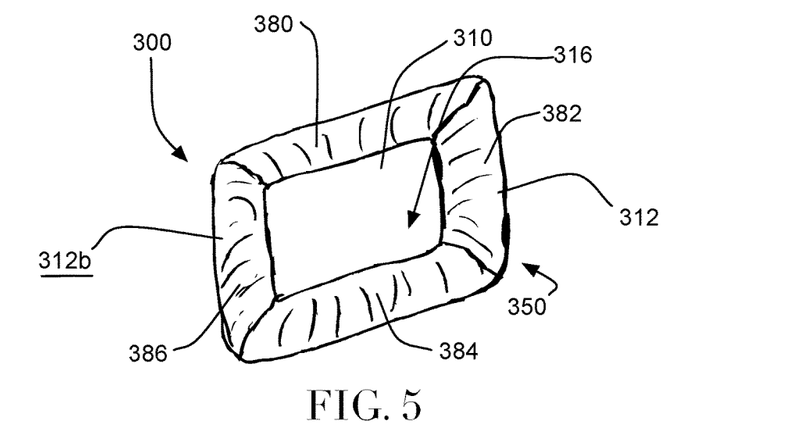
FIG. 5 is a perspective view of another example medical device.
Figure 6:
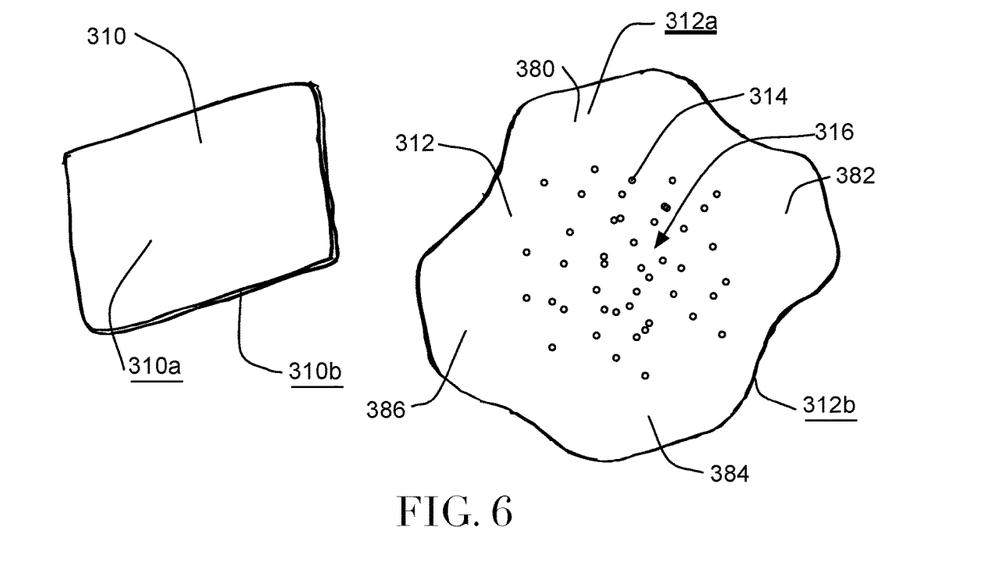
FIG. 6 is an exploded view of the medical device illustrated in FIG. 5.

FIGS. 5 and 6 illustrate a third example medical device 300. The medical device 300 according to this embodiment is similar to the medical device 100 described above and illustrated in FIGS. 1 through 3, except as detailed below. Thus, medical device 300 comprises first 310 and second 312 layers and a bioactive 314 disposed between the layers 310, 312. In this embodiment, as best illustrated in FIG. 6, a solution containing the bioactive 314 has been disposed onto a surface 312a of the second layer 312 and the bioactive 314 has diffused into the material of the layer 312 (represented by the open circles in the FIG. 6) prior to final assembly of the medical device 300.

The first layer 310 has a first surface 310a and a second surface 310b. Similarly, the second layer 312 has a first surface 312a and a second surface 312b. The first layer 310 is rectangular in shape. In this embodiment, the second layer 312 has a rectangular central portion 316 and first 380, second 382, third 384 and fourth 386 peripheral tabs extending outwardly from the central portion 316. The second layer 312 is larger than the first layer 310 allowing the peripheral tabs 380, 382, 384, 386 of the second layer 312 to be folded over peripheral portions of the first layer 310 and into contact with the first surface 310a of the first layer once the first layer 310 is disposed on the second layer 312. This structural configuration provides a triple laminate structure 350 that extends continuously around the entire peripheral edge of the medical device 300.

The structure provided by a medical device having a triple laminate structure that extends continuously around the entire peripheral edge of the medical device may be advantageous for a variety of situations. For example, the structure can be used to limit, and even prevent, if desired, lateral release of the bioactive from the peripheral edges of the medical device while permitting release of the bioactive from the exposed portion of the first layer. This provides a great deal of control over the direction in which the bioactive will be released at a point of treatment, allowing a user to focus the bioactive and its treatment effects on a particular location while having confidence that adjacent locations will have limited to no exposure to the bioactive.

Figure 7:
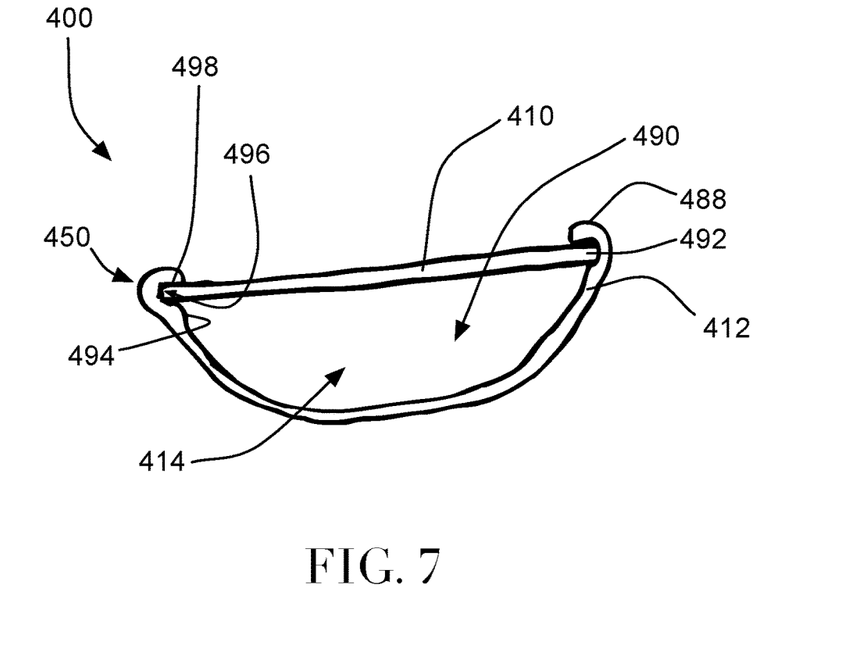
FIG. 7 is a sectional view of another example medical device.

FIG. 7 illustrates a fourth example medical device 400. The medical device 400 according to this embodiment is similar to the medical device 300 described above and illustrated in FIGS. 5 and 6, except as detailed below. Thus, medical device 400 comprises first 410 and second 412 layers and a bioactive 414 disposed between the layers 410, 412.

In this embodiment, a cavity 490 is disposed between the layers 410, 412 and the bioactive 414 is disposed in the cavity 490. In the illustrated embodiment, a powder containing the bioactive 414 occupies the entire space of the cavity 490. It is noted, though, that the cavity 490 in a medical device according to a particular embodiment can be partially filled with a powder containing a bioactive or with another substance or solution containing the bioactive. Leaving some of the space of the cavity unfilled may be advantageous if it is desired to provide a medical device that can be physically manipulated to a greater degree, such as a medical device intended to be used at points of treatment that typically have greater degrees of physical variability between patients, for example.

In this embodiment, each of the first layer 410 and the second layer 412 is circular in shape. The second layer 412 is larger than the first layer 410, allowing a peripheral portion 488 of the second layer 412 to be folded over a peripheral portion 492 of the first layer 410 once the bioactive 414 has been placed and the first layer 410 has been disposed over the second layer 412 and the bioactive 414. The second layer 414 defines a circumferential shoulder 494 and a circumferential groove 496 that receives the peripheral edge 498 of the first layer. This structural configuration provides a triple laminate structure 450 that extends continuously around the peripheral edge of the medical device 400. Also, the medical device 400 has an overall bowl-shaped configuration.

The structure provided by a medical device having a cavity disposed between the first and second layers may be advantageous for situations in which it is desirable to have a medical device that is adapted to fill a void or other space at a point of treatment, such as in an abdominal cavity or interstitial space of a human patient.

Methods

Figure 8:
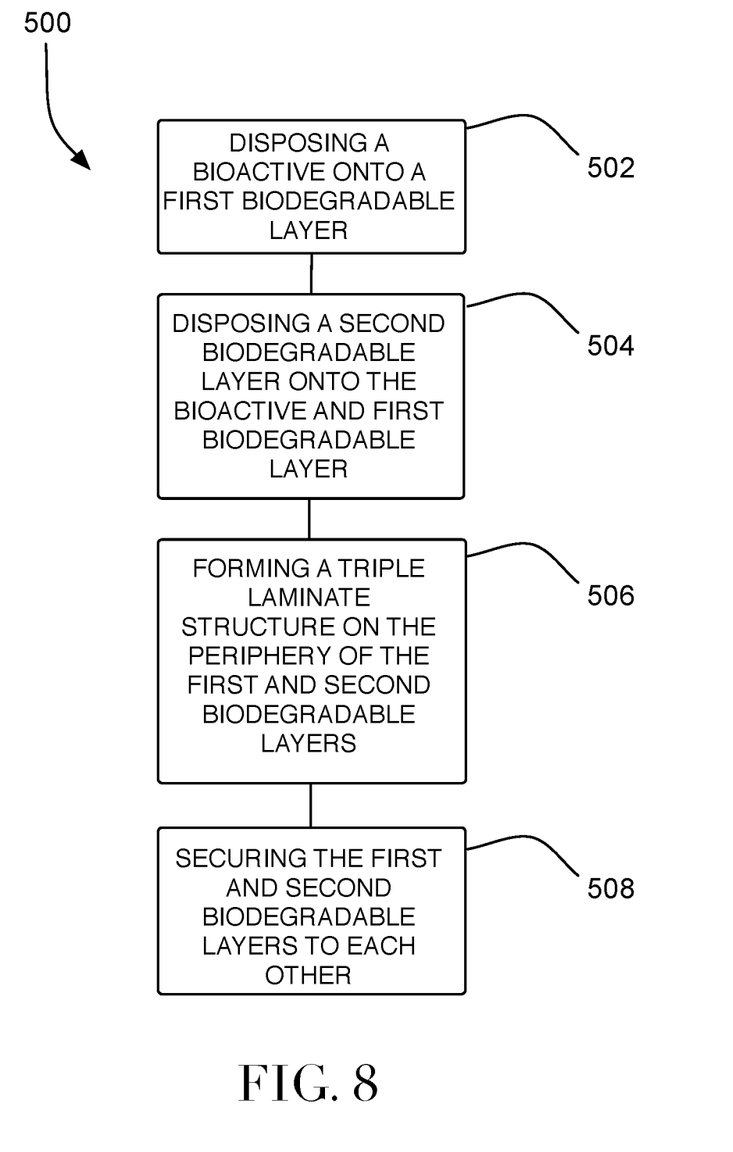
FIG. 8 is a schematic illustration of an example method of making a medical device.

FIG. 8 illustrates an example method 500 of making a medical device for delivering a bioactive. A step 502 comprises disposing a bioactive onto a first biodegradable layer. Another step 504 comprises disposing a second biodegradable layer onto the bioactive and first biodegradable layer. An optional step 506 comprises forming a triple laminate structure on the periphery of the first and second biodegradable layers. Another step 508 comprises securing the first and second biodegradable layers to each other.

The invention also includes the medical devices made by performance of the methods described herein. One example medical device comprises a medical device made by a method of making a medical device for delivering a bioactive, the method comprising disposing a bioactive onto a first biodegradable layer; disposing a second biodegradable layer onto the bioactive and first biodegradable layer; and securing the first and second biodegradable layers to each other.

The method can optionally include forming a triple laminate structure on the periphery of the first and second biodegradable layers.

The invention also includes methods of using the medical devices described herein, such as by placing a medical device described herein into a body at a point of treatment, such as a point of treatment in a body cavity in contact with one or more margins of a resected tumor. Also, the invention includes methods of using the medical devices described herein in combination with another medical device, such as by placing a medical device described herein around a stent, such as an esophageal stent, and placing the medical devices together into a body at a point of treatment, such as a point of treatment in an esophagus of an animal. In this manner, the medical device is sandwiched between the tissue at the point of treatment and the stent.

It is noted that, in all methods, individual steps can be performed in any suitable order. For example, in a method that includes a step of massaging the substrate, the massaging step can be performed during the step of initiating flow of the solution toward the substrate, after completion of the step of initiating flow of the solution toward the substrate, or repeatedly and alternatively with several steps of initiating flow of the solution toward the substrate.

The methods described herein provide flexibility in the performance of treatment procedures. The methods can be performed in anticipation of performance of a treatment procedure on a patient that uses a medical device made by the method. For example, a pharmacy can perform a particular method to prepare a medical device for use in the treatment procedure hours, days or even weeks before the treatment procedure is to be performed. The medical device made by the method can be stored in suitable packaging and made available at the time of the treatment procedure. Also, the methods can be performed immediately prior to performance of a treatment procedure on a patient that uses a medical device made by the method. Indeed, the methods described herein can be performed bedside in a hospital, immediately before use of the resulting medical device on a particular patient. In cancer treatment procedures, for example, this allows a caregiver to select a desired chemotherapeutic bioactive or immunotherapeutic bioactive for local delivery for a particular patient and then perform a method of making a medical device, such as one of the methods described herein, or instruct another to perform a method of making a medical device, and then use the resulting medical device in the immediate treatment for the particular patient.

While various example medical devices and method are described with reference to specific features of particular drawings, it is understood that the various elements, steps and/or features described herein in connection with one particular example can be combined with those of another without departing from the scope of the invention. Furthermore, the medical devices and methods described and illustrated herein provide examples of the invention, and are not intended to limit the scope of the invention in any manner. Rather, they serve only to aid those skilled in the art to perform, make and use the invention.

We claim:

1. A medical device for delivering a bioactive, said medical device comprising:
   a first biodegradable layer having a first peripheral edge, first and second opposing surfaces, and a first peripheral portion including portions of the first and second opposing surfaces and a portion of the first peripheral edge, the first layer having a first area;

a second biodegradable layer having a second peripheral edge, third and fourth opposing surfaces, and a second peripheral portion including portions of the third and fourth opposing surfaces and a portion of the second peripheral edge, the second layer having a second area that is less than the first area;

the first and second biodegradable layers positioned such that the second surface faces the third surface;

the first peripheral portion folded over the second peripheral portion to form a triple laminate structure in which a portion of the second surface contacts a portion of the fourth surface; and a bioactive disposed between the first and second biodegradable layers.

2. The medical device of claim 1, wherein the first and second biodegradable layers are formed of the same material.

3. The medical device of claim 1, wherein the first and second biodegradable layers are formed of different materials.

4. The medical device of claim 3, wherein one of the first and second biodegradable layers is formed of a first biodegradable material and the other of the first and second biodegradable layers is formed of a second biodegradable material; and
wherein the first biodegradable material degrades relatively quickly in vivo and the second biodegradable material degrades relatively slowly in vivo.

5. The medical device of claim 1, wherein one of the first and second biodegradable layers is formed of a cellulose material.

6. The medical device of claim 5, wherein the cellulose material comprises carboxymethyl cellulose.

7. The medical device of claim 5, wherein the cellulose material comprises Hydroxylpropyl methyl cellulose.

8. The medical device of claim 1, wherein the first biodegradable layer is secured to the second biodegradable layer.

9. The medical device of claim 1, wherein the first and second biodegradable layers cooperatively define a cavity between the first and second biodegradable layers.

10. The medical device of claim 9, wherein the bioactive is disposed in the cavity.

11. The medical device of claim 10, wherein the bioactive comprises a powder.

12. The medical device of claim 11, wherein the bioactive occupies the entire space of the cavity.

13. The medical device of claim 11, wherein the cavity is partially filled with the bioactive.

14. The medical device of claim 1, wherein the first biodegradable layer includes a main portion and first and second tabs extending from the main portion.

15. The medical device of claim 14, wherein the first peripheral portion comprises the first and second tabs.

16. The medical device of claim 14, wherein the first peripheral portion consists of the first and second tabs.

17. The medical device of claim 1, wherein the triple laminate structure extends along only a single outer edge of said medical device.

18. The medical device of claim 1, wherein the triple laminate structure extends continuously along the entire outer edge of said medical device.

19. A medical device for delivering a bioactive, said medical device comprising:
a first biodegradable layer having a first peripheral edge, first and second opposing surfaces, and a first peripheral portion including portions of the first and second opposing surfaces and the entire first peripheral edge, the first layer having a first area;

a second biodegradable layer having a second peripheral edge, third and fourth opposing surfaces, and a second peripheral portion including portions of the third and fourth opposing surfaces and the entire second peripheral edge, the second layer having a second area that is less than the first area;

the first and second biodegradable layers positioned such that the second surface faces the third surface;

the first peripheral portion folded over the second peripheral portion to form a triple laminate structure extending continuously along the entire outer edge of said medical device such that a portion of the second surface contacts a portion of the fourth surface; and a bioactive disposed between the first and second biodegradable layers.

20. A medical device for delivering a bioactive, said medical device comprising:
a first biodegradable layer having a first peripheral edge, first and second opposing surfaces, and a first peripheral portion including portions of the first and second opposing surfaces and the entire first peripheral edge, the first layer having a first area;

a second biodegradable layer having a second peripheral edge, third and fourth opposing surfaces, and a second peripheral portion including portions of the third and fourth opposing surfaces and the entire second peripheral edge, the second layer having a second area that is less than the first area;

the first and second biodegradable layers positioned such that the second surface faces the third surface and the first and second biodegradable layers cooperatively define a cavity between the first and second biodegradable layers;

the first peripheral portion folded over the second peripheral portion to form a triple laminate structure extending continuously along the entire outer edge of said medical device such that a portion of the second surface contacts a portion of the fourth surface; and a bioactive disposed in the cavity between the first and second biodegradable layers.

* * * * *